US008080041B2

(12) United States Patent
Boehm, Jr. et al.

(10) Patent No.: US 8,080,041 B2
(45) Date of Patent: Dec. 20, 2011

(54) DEVICE AND METHOD FOR LUMBAR INTERBODY FUSION

(75) Inventors: Frank H. Boehm, Jr., Utica, NY (US); Benedetta Delorenzo Melnick, Rome, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 173 days.

(21) Appl. No.: 12/221,039

(22) Filed: Jul. 30, 2008

(65) Prior Publication Data
US 2008/0294171 A1    Nov. 27, 2008

Related U.S. Application Data

(60) Continuation of application No. 10/798,145, filed on Mar. 11, 2004, now abandoned, which is a continuation of application No. 10/365,187, filed on Feb. 12, 2003, now Pat. No. 6,730,126, which is a division of application No. 10/010,314, filed on Nov. 13, 2001, now Pat. No. 6,666,891.

(60) Provisional application No. 60/248,137, filed on Nov. 13, 2000.

(51) Int. Cl.
*A61B 17/88* (2006.01)
(52) U.S. Cl. .......................... 606/279; 606/99
(58) Field of Classification Search .................. 623/908, 623/7.11–17.161; 606/90, 99, 104, 248–249, 606/279, 191, 198–199, 914; 604/104, 96.01, 604/164.1, 114; 600/204, 201; D24/135
See application file for complete search history.

(56) References Cited

U.S. PATENT DOCUMENTS

| | | | | |
|---|---|---|---|---|
| 3,811,449 A | * | 5/1974 | Gravlee et al. | 606/191 |
| 4,449,532 A | | 5/1984 | Storz | |
| 4,545,374 A | | 10/1985 | Jacobson | |
| 4,573,448 A | | 3/1986 | Kambin | |
| 4,862,891 A | * | 9/1989 | Smith | 606/191 |
| 4,968,315 A | | 11/1990 | Gatturna | |
| 4,978,334 A | * | 12/1990 | Toye et al. | 604/506 |
| 4,994,027 A | | 2/1991 | Farrell | |
| 5,015,247 A | | 5/1991 | Michelson | |

(Continued)

FOREIGN PATENT DOCUMENTS
DE    44 16 605    11/1994

(Continued)

*Primary Examiner* — Thomas C. Barrett
*Assistant Examiner* — Christian Sevilla

(57) ABSTRACT

A method for performing percutaneous interbody fusion is disclosed. The method includes the steps of inserting a guide needle posteriorly to the disc space, inserting a dilator having an inner diameter slightly larger than the outer diameter of the guide needle over the guide needle to the disc space to enlarge the disc space, and successively passing a series of dilators, each having an inner diameter slightly larger than the outer diameter of the previous dilator, over the previous dilator to the disc space the gradually and incrementally increase the height of the disc space. Once the desired disc height is achieved, the guide needle and all the dilators, with the exception of the outermost dilator, are removed. An expandable intervertebral disc spacer is then passed through the remaining dilator and positioned in the disc space. The disc spacer is expanded to the required disc height, and then a bone matrix is passed through the dilator to fill the disc space. The dilator is then removed. An expandable intervertebral disc spacer is also disclosed, having a tapered bore that causes greater expansion of one end of the spacer with respect to the other. A kit for performing the percutaneous interbody fusion procedure is also disclosed.

27 Claims, 4 Drawing Sheets

U.S. PATENT DOCUMENTS

| | | | |
|---|---|---|---|
| 5,071,410 A | | 12/1991 | Pazell |
| 5,158,543 A | * | 10/1992 | Lazarus ..................... 604/164.1 |
| 5,171,279 A | | 12/1992 | Mathews |
| 5,312,360 A | | 5/1994 | Behl |
| 5,357,983 A | | 10/1994 | Mathews |
| 5,472,426 A | * | 12/1995 | Bonati et al. ................ 604/164.1 |
| 5,484,437 A | | 1/1996 | Michelson |
| 5,496,322 A | | 3/1996 | Mathews |
| 5,522,899 A | | 6/1996 | Michelson |
| 5,609,635 A | | 3/1997 | Michelson |
| 5,665,122 A | | 9/1997 | Kambin |
| 5,741,253 A | | 4/1998 | Michelson |
| 5,752,969 A | | 5/1998 | Cunci |
| 5,762,629 A | * | 6/1998 | Kambin .................... 604/164.11 |
| 5,782,832 A | | 7/1998 | Larsen et al. |
| 5,792,044 A | * | 8/1998 | Foley et al. ................... 600/114 |
| 5,803,904 A | | 9/1998 | Mehdizadeh |
| 5,817,034 A | | 10/1998 | Milliman et al. |
| 5,888,228 A | | 3/1999 | Knothe et al. |
| 5,902,231 A | | 5/1999 | Foley et al. |
| 5,954,671 A | | 9/1999 | O'Neill |
| 5,964,781 A | | 10/1999 | Mollenauer et al. |
| 5,984,967 A | | 11/1999 | Zdeblick et al. |
| 6,042,582 A | | 3/2000 | Ray |
| 6,063,121 A | | 5/2000 | Xavier et al. |
| 6,080,155 A | | 6/2000 | Michelson |
| 6,080,193 A | | 6/2000 | Hochshuler et al. |
| 6,083,225 A | | 7/2000 | Winslow et al. |
| 6,096,038 A | | 8/2000 | Michelson |
| 6,113,602 A | | 9/2000 | Sand |
| 6,117,174 A | | 9/2000 | Nolan |
| 6,126,689 A | | 10/2000 | Brett |
| 6,129,763 A | | 10/2000 | Chauvin et al. |
| 6,156,040 A | | 12/2000 | Yonemura et al. |
| 6,162,170 A | | 12/2000 | Foley et al. |
| 6,186,986 B1 | * | 2/2001 | Berg et al. ..................... 604/264 |
| 6,197,033 B1 | | 3/2001 | Haid, Jr. et al. |
| 6,200,322 B1 | | 3/2001 | Branch et al. |
| 6,206,923 B1 | * | 3/2001 | Boyd et al. ................. 623/17.11 |
| 6,213,957 B1 | | 4/2001 | Milliman et al. |
| 6,224,595 B1 | | 5/2001 | Michelson |
| 6,224,607 B1 | * | 5/2001 | Michelson .................... 606/96 |
| 6,241,769 B1 | | 6/2001 | Nicholson et al. |
| 6,245,072 B1 | | 6/2001 | Zdeblick et al. |
| 6,270,498 B1 | | 8/2001 | Michelson |
| 6,375,655 B1 | | 4/2002 | Zdeblick et al. |
| 6,395,034 B1 | | 5/2002 | Suddaby |
| 6,419,705 B1 | | 7/2002 | Erickson |
| 6,436,098 B1 | | 8/2002 | Michelson |
| 6,436,142 B1 | * | 8/2002 | Paes et al. ................... 623/17.15 |
| 6,454,807 B1 | | 9/2002 | Jackson |
| 6,520,907 B1 | | 2/2003 | Foley et al. |
| 6,527,734 B2 | | 3/2003 | Cragg et al. |
| 6,562,046 B2 | | 5/2003 | Sasso |
| 6,565,574 B2 | | 5/2003 | Michelson |
| 6,575,899 B1 | | 6/2003 | Foley et al. |
| 6,575,979 B1 | | 6/2003 | Cragg |
| 6,648,917 B2 | | 11/2003 | Gerbec et al. |
| 6,666,891 B2 | * | 12/2003 | Boehm et al. ............... 623/17.16 |
| 6,916,330 B2 | * | 7/2005 | Simonson ..................... 606/191 |
| 2001/0012950 A1 | | 8/2001 | Nishtaka et al. |
| 2002/0002360 A1 | | 1/2002 | Orth et al. |
| 2002/0032483 A1 | | 3/2002 | Nicholson et al. |
| 2002/0077641 A1 | | 6/2002 | Michelson |
| 2002/0087152 A1 | | 7/2002 | Mikus et al. |
| 2002/0107574 A1 | | 8/2002 | Boehm, Jr. et al. |
| 2002/0133128 A1 | | 9/2002 | Heller |
| 2002/0138146 A1 | | 9/2002 | Jackson |
| 2003/0073998 A1 | | 4/2003 | Pagliuca et al. |
| 2003/0083688 A1 | | 5/2003 | Simonson |
| 2003/0083689 A1 | | 5/2003 | Simonson |
| 2003/0139814 A1 | | 7/2003 | Bryan |
| 2003/0176926 A1 | | 9/2003 | Boehm et al. |

FOREIGN PATENT DOCUMENTS

| | | |
|---|---|---|
| EP | 0 077 159 | 10/1982 |
| EP | 0 712 607 | 5/1996 |
| EP | 1 129 668 | 9/2001 |
| EP | 1 153 574 | 11/2001 |
| EP | 1 219 268 | 7/2002 |
| FR | 98 10832 | 8/1998 |
| WO | WO 96/27321 | 9/1996 |
| WO | WO 00/24326 | 5/2000 |
| WO | WO 00/35388 | 6/2000 |
| WO | WO 00/42898 | 7/2000 |
| WO | WO 00/49977 | 8/2000 |
| WO | WO 00/61011 | 10/2000 |
| WO | WO 01/12080 | 2/2001 |
| WO | WO 02/067786 | 9/2002 |

* cited by examiner

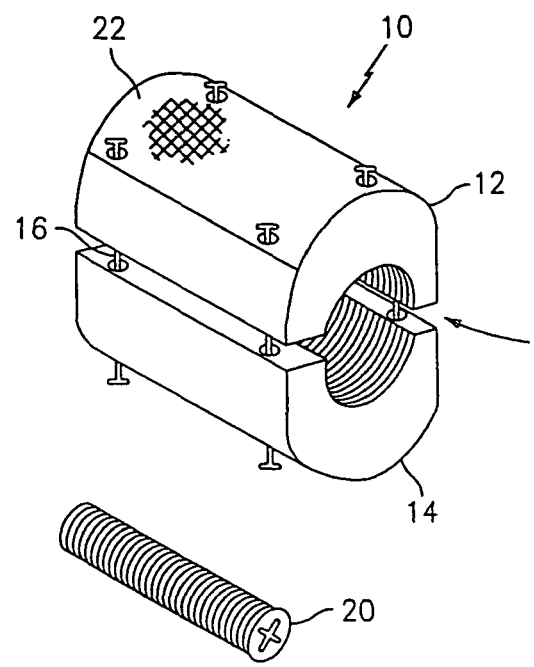
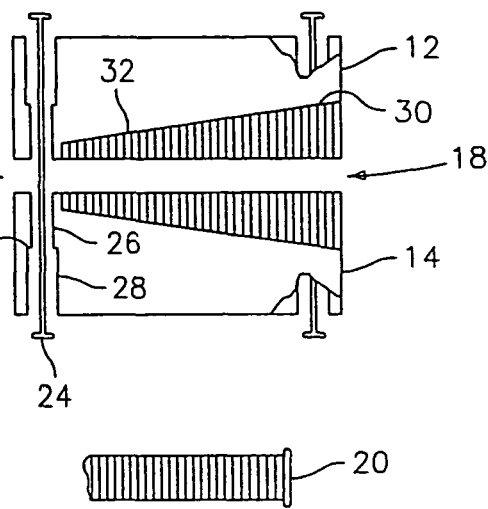
FIG. 1
FIG. 2
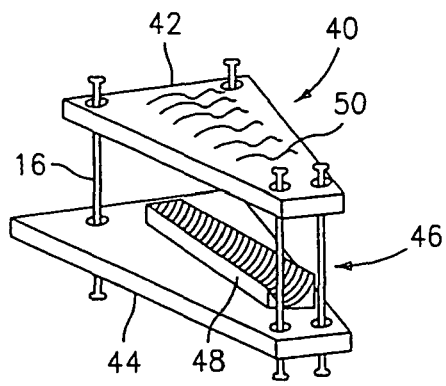
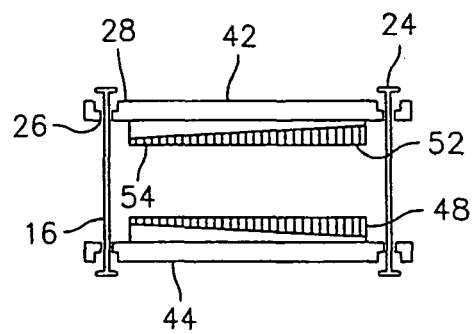
FIG. 3
FIG. 4

DEVICE AND METHOD FOR LUMBAR INTERBODY FUSION

CROSS REFERENCE TO RELATED APPLICATIONS

The present application is a continuation of U.S. patent application Ser. No. 10/798,145 filed Mar. 11, 2004, now abandoned, which is a continuation of U.S. patent application Ser. No. 10/365,187 filed Feb. 12, 2003 and issued as U.S. Pat. No. 6,730,126, which is a divisional of U.S. patent application Ser. No. 10/010,314 filed Nov. 13, 2001 and issued as U.S. Pat. No. 6,666,891, which claims the benefit of U.S. Provisional Patent Application Serial No. 60/248,137 filed Nov. 13, 2000, the contents of each of these applications hereby incorporated by reference in their entirety.

BACKGROUND OF THE INVENTION

1. Field of the Invention

The present invention relates to a device and method for performing interbody spinal fusion, stabilization and restoration of the disc height in the spine, and in particular to a device and method for performing percutaneous, minimally invasive interbody fusion of the lumbar spine.

2. Discussion of the Related Art

Many devices exist to assist in maintaining the position of the lumbar vertebra in conjunction with lumbar fusion surgery. Fusion is the joining together of the vertebra of the spine. The underlying concept of the known devices is to maintain the relative position of the vertebral bodies with respect to each other, while the bone that has been placed between the vertebra to form the fusion of the vertebra, has an opportunity to heal and mature. These devices employ different strategies and philosophies, and can include devices which utilize the pedicles, as well as devices which are placed in to the disc space to promote fusion across the disc space. The latter devices and techniques associated with these devices are known as "interbody fusion". While no single technique has been universally accepted as the most optimum method, there is growing evidence that interbody fusion may be the preferred method.

The interbody fusion procedure may be performed via an anterior or posterior approach. Initially, all interbody fusion procedures were accomplished using the posterior approach. The procedure was performed by first performing a laminectomy, removing the disc space, and then packing the disc space with pieces of bone, which were then permitted to heal over time. The hope was that the inserted bone pieces would grow and fuse together with the vertebra above and below that disc space, forming a bridge of bone between the two vertebral bodies, thus accomplishing the interbody fusion.

Posterior interbody fusion procedures are accomplished via a variety of techniques. Most procedures attempt to restore proper disc height, i.e. the space between the adjacent vertebra. The patient benefits from restoring the proper disc height, particularly where there has been deterioration, degeneration or collapse of the disc.

More recently, the anterior interbody fusion procedure has gained popularity, due to the availability and improvements made in devices that enable the anterior approach for lumbar interbody fusions. These devices typically provide for a retroperitoneal or transperitoneal technique to be used for approaching the lumbar disc, removing some or all of the disc, and placing either bone or a metallic device into the disc space. These devices also typically provide a means for distracting the disc space, i.e. making the space between the discs wider. Presently, this aspect of lumbar interbody fusion procedures are considered to be an important step in the procedure because of its effects on the neural foramina, or areas from which the nerve roots exit through the vertebra. It is generally accepted that enlarging the disc space consequently enlarges the neural foramina, thus decompressing the exiting nerve roots.

The current techniques, due to the present equipment available, particularly for anterior interbody fusion, suffer the disadvantage in that they are major surgeries and require large incisions with the manipulation of both tissue and organs. While attempts have been made to perform anterior interbody fusions laparoscopically, these procedures are often complicated and are typically performed under general anesthesia.

Therefore, a need exists for a method for performing interbody fusions that reduces the trauma to the patient, and consequently reducing recovery time. A device is also needed to facilitate the interbody fusion procedure to enable the procedure to be performed percutaneously, enabling the surgeon to distract the disc to restore disc height, maintain the distraction, and promote the growth of the bone placed in the disc space between the two vertebral bodies, thus accomplishing the interbody fusion.

SUMMARY OF THE INVENTION

It is, therefore, an object of the present invention to provide a minimally invasive, percutaneous surgical procedure for performing interbody fusion which reduces the trauma to the patient and reduces recovery time.

It is also an object of the present invention to provide a percutaneous interbody fusion procedure which accomplishes the interbody fusion through small incisions in the body of the patient and utilizes a minimum of incisions to complete the procedure.

It is a further object of the present invention to provide a device which facilitates the percutaneous interbody fusion procedure.

It is yet another object of the present invention to provide a device which distracts the disc space and which may be inserted through a tube to effect the percutaneous interbody fusion procedure.

It is a further object of the present invention to provide a collapsible and expandable interbody fusion spacing device that facilitates the percutaneous interbody fusion procedure.

It is still a further object of the present invention to provide a kit for performing a minimally invasive percutaneous interbody fusion procedure.

The above and other objects of the present invention may be achieved by providing a collapsible and expandable interbody fusion spacer device that may be inserted through a small diameter tube to the disc space that is being fused, so that the procedure may be performed in a minimally invasive manner. The spacer is preferably constructed in two halves that are connected by pins located on the sides of the spacer. The outer surface may be flat to engage the end plate of the vertebra above and below the spacer, and the outer surface may be scored, have ridges, points, tabs, detents, or the like to enhance gripping of the end plates of the vertebra to resist movement of the spacer once it is in place. The interior surfaces of the halves that make up the spacer include a semicircular hollowed portion that is preferably threaded along at least a portion of its length that is aligned with a similar semicircular threaded hollowed portion on the other half of the spacer. When the spacer is assembled, the threaded portion forms a canal for acceptance of a piston screw. Preferably, the threaded canal is tapered from one end to the other, particularly from the end which will be positioned posteriorly in the disc space to the end which will be positioned anteriorly in the disc space. When the piston screw is inserted, the anteriorly positioned end will expand a greater distance in the disc space than the posterior end, due to the tapered threaded canal. This will cause the disc height, i.e. the distance between the vertebra, to be greater anteriorly than posteriorly, which more closely mimics the natural curve of the spine, particularly in the lumbar spine, thus restoring lordosis, the natural curve of the lumbar spine.

A method for performing percutaneous interbody fusion is also provided, in which the disc space is enlarged in the craniocaudal direction following percutaneous discectomy. Following the discectomy, a guide needle is passed through the incision to the disc space between the vertebra. Over the needle, a series of tubularly shaped dilators are passed, with each successive dilator having an inner diameter that is slightly larger than the outer diameter of the dilator that is in place. As each successive dilator is inserted in the disc space, it forces the vertebra apart, increasing the disc space, until a desired height between the vertebra is achieved. Once a desired height is reached, which is only a desired height and not necessarily the maximum height, the outer dilator is left in place, while those inside the outer dilator are removed. The maximum height does not have to be achieved by the dilators because the expandable intervertebral disc spacer of the present invention is then inserted into the disc space through the outer dilator. Once in place, the spacer is expanded to increase the disc height to the maximum distance. After the spacer is in place on one side of the vertebral body, the procedure is repeated on the other side. After the two spacers are in place, a bone matrix, which encourages fusion, is passed through the dilators, filling the space with bone. The dilators are then removed and the procedure is complete.

A kit for performing percutaneous interbody fusion is also provided, which includes a plurality of expandable intervertebral disc spacers, which preferably expand the disc space a greater distance anteriorly than posteriorly, at least one dilator for expanding the disc height and having a hollow interior for allowing passage of the disc spacers to the disc space, and a guide needle. A curette for performing percutaneous discectomies may be provided, and a bone matrix for fusing the vertebra together may also be provided.

BRIEF DESCRIPTION OF THE DRAWINGS

The above and other objects, features and advantages of the present invention will become more readily apparent from the following detailed description of preferred embodiments of the invention, taken in conjunction with the accompanying drawings, in which:

FIG. 1 illustrates a perspective view of an expandable intervertebral disc spacer according to the present invention;

FIG. 2 illustrates a side cross-sectional view of the disc spacer of FIG. 1;

FIG. 3 illustrates a perspective view of an alternative embodiment of the expandable intervertebral disc spacer of FIG. 1;

FIG. 4 illustrates a side cross-sectional view of the disc spacer of FIG. 3;

DETAILED DESCRIPTION OF THE PREFERRED EMBODIMENTS

Figure 5:
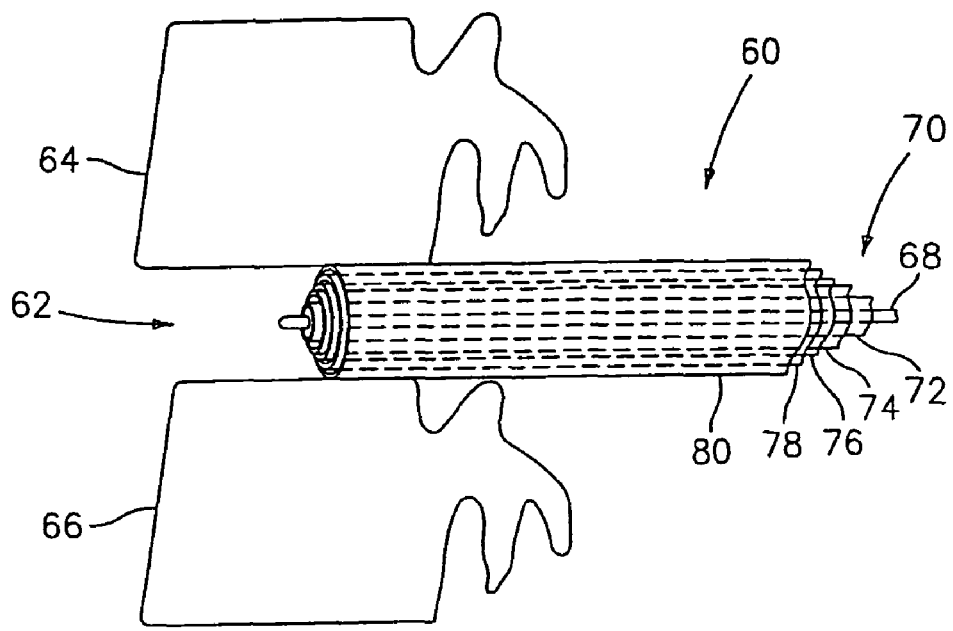
FIG. 5 illustrates diagrammatic view of a dilator system for enlarging the disc height of the vertebra prior to placement of the disc spacer of the present invention between the vertebra.

Referring now to the drawings, in which like reference numerals identify similar or identical elements throughout the several views, and inn particular to FIG. 1, there is shown the expandable intervertebral disc spacer device 10 according to the present invention. Preferably, the disc spacer 10 is comprised of two similarly shaped halves 12, 14 that are opposed to each other and loosely connected by pins 16. The outer surface of each half may be scored, as indicted by reference numeral 22, for facilitating adherence to the end plates of the vertebral bodies between which disc spacer 10 is placed. When top half 12 and bottom half 14 are assembled, together they may form a cylinder, a cube, a rectangular box, or any geometric shape that may be split to form two opposed halves. A tapered bore 18 is provided, which has a larger diameter 30 at a first end and a smaller diameter 32 at a second end. Preferably, tapered bore 18 is threaded over at least a portion of its length. While disc spacer 10 is preferably constructed of titanium or other suitable metal alloy, cortical bone may also be used. It is also contemplated that the material of the disc spacer 10, or at least the material of which tapered bore 18 is constructed, is self-tapping so that threads are not needed.

Screw 20 is provided for insertion into bore 18 to expand the disc spacer 10. As seen in FIG. 2, pins 16 are located in pin bores 26 which have a larger diameter near the outer surface of disc spacer 10, and a smaller diameter near the interior of the spacer. The change in diameter creates a stop 34 which engages the head 24 of pins 16, to terminate expansion of the spacer 10. When screw 20 is inserted into bore 18, the smaller diameter 32 of the threaded bore causes a greater expansion at the second end than at the first, for reasons which will be described below.

FIGS. 3 and 4 illustrate an alternative embodiment of the disc spacer 40 of the present invention. Disc spacer 40 comprises a pair of opposed plates 42, 44 which may be square, rectangular, rhomboidal, trapezoidal, or any suitable geometric shape. Pins 16 loosely hold the plates together, as described above, through pin bores 26, which include larger diameter portion 28 which creates stop 34 to engage the head 24 of pins 16. The outer surface of plates 42, 44 may include ridges 50, detents, scoring or the like to enhance adherence to the end plates of the vertebra. Each plate includes a threaded ledge portion 48, which forms a bore for accepting screw 20 when the plates are assembled to form disc spacer 40. Preferably, the threaded portion has a larger diameter at a first end 52 and a smaller diameter at a second end 54, so that there is greater expansion of the spacer at the second end 54 than at first end 52, for reasons which will be described below.

Figure 6:
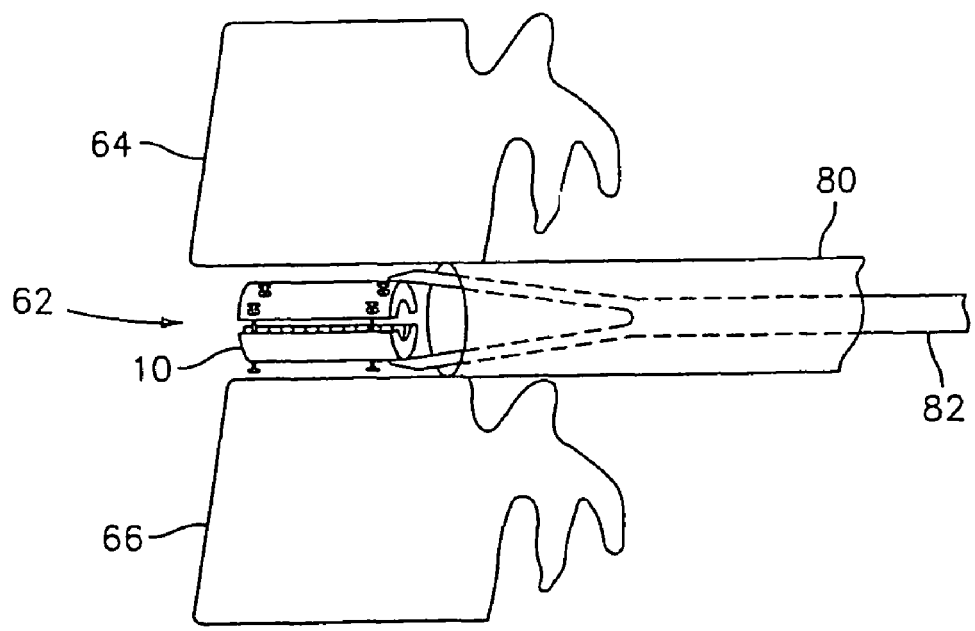
FIG. 6 illustrates a diagrammatic view of the placement procedure of the disc spacer of the present invention.
Figure 7:
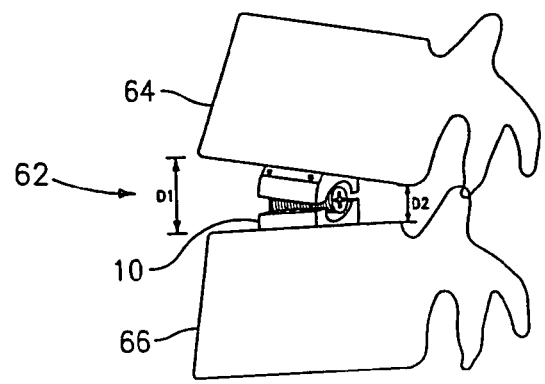
FIG. 7 illustrates a diagrammatic view of the disc spacer in place between the vertebra and in a fully expanded condition to restore the natural curvature of the spine.

FIGS. 5, 6 and 7 illustrate the percutaneous interbody fusion procedure of the present invention, utilizing the expandable intervertebral disc spacer of the present invention. Following a percutaneous discectomy in which the disc between vertebra 64 and 66 is removed, preferably posteriorly, through a small incision, disc space 62 is enlarged using dilator system 60 in the procedure according to the present invention. In the procedure, a guide needle 68 is inserted into the disc space under scanning imaging, preferably fluoroscopy. Once the guide needle 68 is in place in the disc space 62, a series of dilators 70 are inserted over guide needle to enlarge the disc space. A first dilator 72, having an inner diameter that is slightly larger than the outer diameter of guide needle 68 is passed over the guide needle through the incision until it reaches the disc space 62. A second dilator 74, having an inner diameter that is slightly larger than the outer diameter of first dilator 72 is then passed over dilator 72 until it reaches disc space 62. A third dilator 76, a fourth dilator 78 and a fifth dilator 80, each having successively larger inner diameters, are then passed over the previous dilator into the disc space 62. As each dilator enters the disc space, it gradually and incrementally enlarges the height of disc space 62 until the disc space is at a desired height. The desired height does not have to be the maximum required height, since that height may be reached by the expandable disc spacer which will be inserted into the disc space. The number of dilators may of course vary, depending on the height of the disc space desired. The depth to which the dilators are inserted can be monitored in many known ways, such as by fluoroscopy, calibrations on the dilators, a combination of both, or other means.

Referring to FIG. 6, once the dilators are in place, and the disc space 62 is at the desired height, the guide needle 68 and all the dilators, with exception of the outermost dilator 80, are removed. Expandable intervertebral disc spacer 10 is the passed through dilator 80 to the disc space 62 by an insertion tool 82. The position of disc spacer 10 is confirmed under fluoroscopy, and either tool 82 or another tool inserted through dilator 80 is used to tighten screw 20. Disc spacer 10 is positioned so that the first end of spacer 10, having the larger diameter 30 of tapered bore 18, is positioned posteriorly, while the second end having smaller diameter 32 of bore 18 is positioned anteriorly. As seen in FIG. 7, when the screw 20 is tightened, the second end, on the anterior side of the spine, opens a distance D2, which is greater than distance D1, which is on the posterior side of the spine. This restores lordosis, or the natural curvature of the spine, particularly in the lumbar region, and relieves the intervertebral foramina and decompresses the nerve roots. Once the disc spacer 10 is in position, bone matrix is passed through the dilator 80 to encourage fusion, to fill the disc space with bone.

While the above procedure has been described for only one set of dilators, and for enlarging the disc space for placement of a disc spacer on one side of the disc space 62, it is understood that the procedure is performed on both sides of the disc space to raise the disc height evenly, and that two disc spacers 10 are inserted. After the bone matrix is inserted, the dilators are then removed and the procedure is complete.

Figure 8:
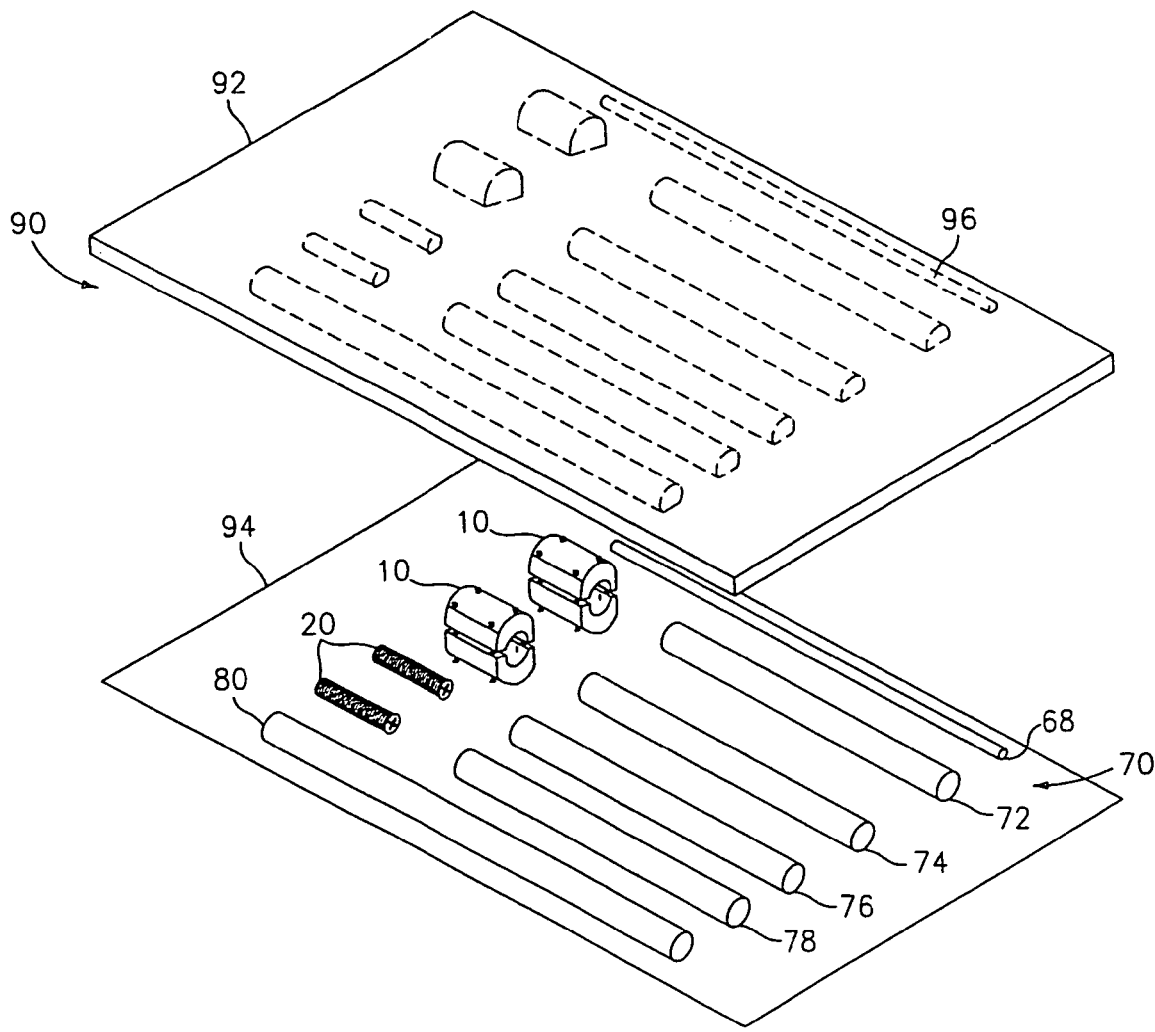
FIG. 8 illustrates a percutaneous interbody fusion kit according to the present invention.

FIG. 8 illustrates a kit for performing the percutaneous interbody fusion procedure of the present invention. Kit 90 comprises a package having top cover 92 and bottom cover 94, where top cover 92 is preferably formed of plastic having depressions or indentations 96 for holding the instruments packaged therein. Packaged in kit 90 are preferably at least two disc spacers 10, a corresponding number of screws 20, a plurality of dilators 70 and a guide needle 68. Kit 90 is preferably sterilized.

Figure 9:
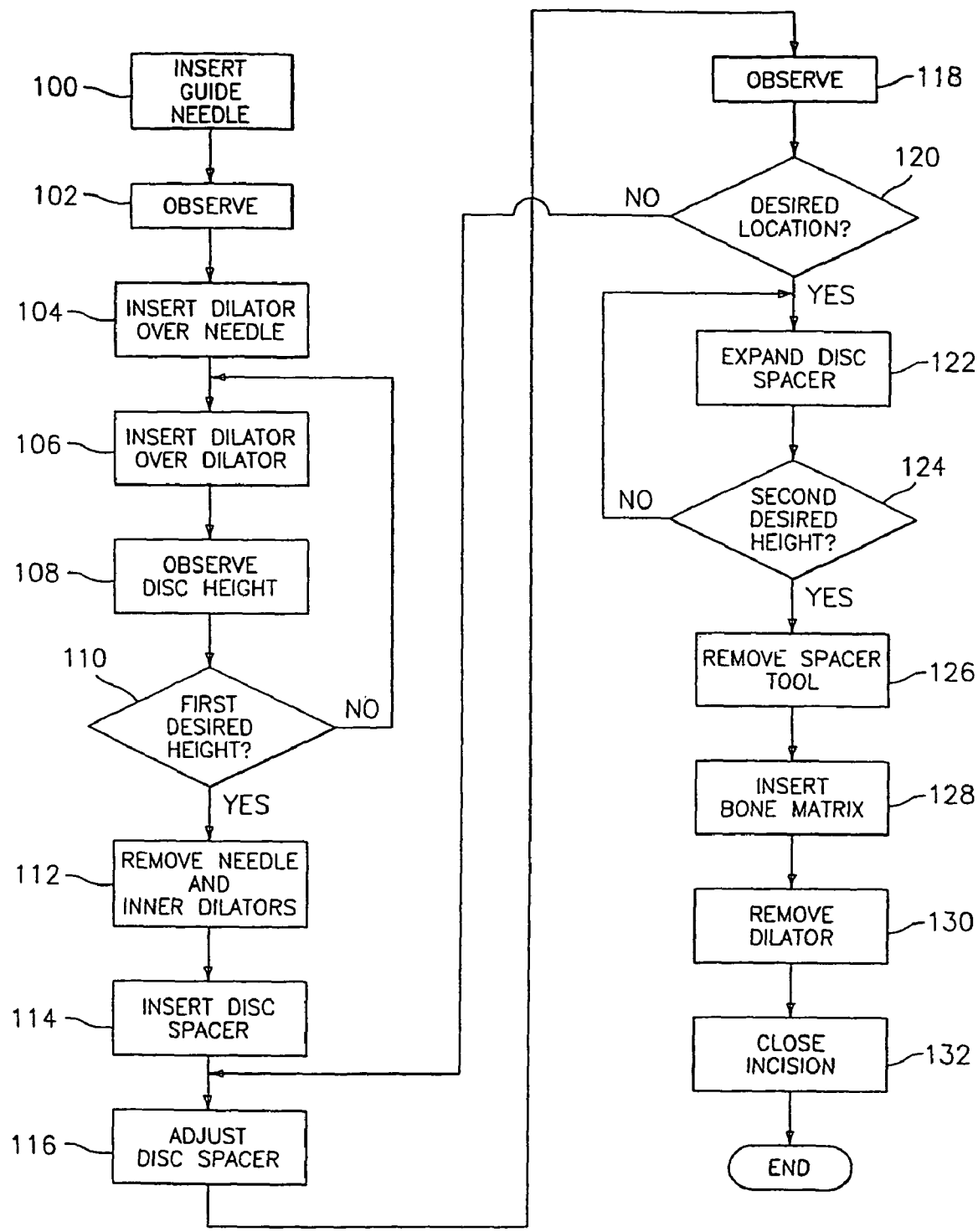
FIG. 9 illustrates a flow chart of the percutaneous interbody fusion method according to the present invention.

FIG. 9 is a flow chart of the method of the present invention. Following a percutaneous discectomy procedure, a guide needle is inserted through the incision at step 100 to the disc space between the vertebral bodies to be fused. The depth to which the guide needle is inserted is observed, preferably through fluoroscopy, in step 102. Once the guide needle is in place, a dilator having an inner diameter that is slightly larger than the outer diameter of the guide needle is passed over the guide needle to the disc space in step 104. The dilator increases the height of the disc space. In step 106, a second dilator is passed over the first dilator, where the second dilator has an inner diameter that is slightly larger than the outer diameter of the first dilator, to further increase or enlarge the disc space. At step 108, the height of the disc space is then observed, preferably through fluoroscopy, to see if it is at the desired height, at step 110. If not, the procedure returns to step 106 and another dilator, having an inner diameter slightly larger than the outer diameter of the previous dilator, is passed over the previous dilator to the disc space. If the disc space is at the desired height, the guide needle and all the dilators, with the exception of the outermost dilator, are removed at step 112. At step 114, an expandable intervertebral disc spacer is inserted through the dilator to the disc space. The position of the disc spacer is adjusted to a proper position at step 116, and then observed, preferably through fluoroscopy, at step 118. If it is determined at step 120 that the disc spacer is not at the correct location, the procedure returns to step 116. If the position is correct, the disc spacer is expanded to enlarge the disc space to a desired height at step 122. If it is determined at step 124 that the space is not at the desired height, the procedure returns to step 122. If the space is at the desired height, the tool is removed at step 126, and a bone matrix is passed down the dilator to the disc space in step 128. Once the bone matrix is in place, the dilator is removed at step 130, and the incision is closed at step 132, ending the procedure.

While the invention has been shown and described with reference to certain preferred embodiments, it will be understood by those skilled in the art that various changes and modifications in form and detail may be made therein without departing from the spirit and scope of the invention, as defined by the appended claims.

What is claimed is:

1. A method for distracting an intervertebral disc space, comprising:
  making a surgical incision;
  providing a first dilator including an outer surface configured to engage endplate surfaces of adjacent vertebrae;
  inserting the first dilator through the surgical incision and into the disc space defined by the endplate surfaces of the adjacent vertebrae such that the outer surface of the first dilator engages the endplate surfaces to distract the endplate surfaces;
  determining if the disc space is at a desired disc space height;
  successively inserting one or more additional dilators over the first dilator and into the disc space such that an outer surface of each of the one or more additional dilators engages the endplate surfaces to distract the endplate surfaces and enlarge the disc space to the desired disc space height; removing each of the dilators except for an outermost dilator; and inserting an intervertebral disc spacer, the intervertebral disc spacer including a screw engageable therewith for expanding the intervertebral disc spacer within the disc space, into the disc space through the outermost dilator.

2. The method of claim 1, further comprising:
  inserting a guide needle through the surgical incision and into the disc space; and wherein the inserting of the first dilator comprises passing the first dilator over the guide needle.

3. The method of claim 1, wherein the inserting of the first dilator into the disc space distracts the disc space to a first disc space height.

4. The method of claim 1, wherein the inserting of the one or more additional dilators into the disc space incrementally distracts the disc space to the desired disc space height.

5. The method of claim 1, wherein each of the dilators has a tubular configuration defining an inner diameter and an outer diameter.

6. The method of claim 5, wherein the inner diameter of each successively inserted dilator is sized slightly larger than the outer diameter of a previously inserted dilator.

7. The method of claim 1, further comprising increasing the desired disc space height to a maximum disc space height after the inserting of the intervertebral disc spacer into the disc space.

8. The method of claim 1, wherein the dilators comprise dilator tubes including distal end portions having sequentially increasing outer diameters; and
wherein the successively inserting comprises successively passing each of the dilator tubes over a preceding dilator tube and inserting the distal end portion of each of the dilator tubes into the disc space and engaging the distal end portion with adjacent vertebrae to incrementally distract a height of the disc space to the desired disc space height.

9. A method for distracting an intervertebral disc space between adjacent vertebrae, comprising:
providing a plurality of dilator tubes, each dilator tube including a proximal end portion, a distal end portion and an outer surface extending therebetween, the plurality of dilator tubes having sequentially increasing outer dimensions;
inserting the outer surface of the distal end portion of a first of the dilator tubes into the disc space and engaging the outer surface of the distal end portion with the endplate surfaces of the adjacent vertebrae to increase the height of the disc space; and successively passing at least one additional dilator tube over a preceding dilator tube and inserting the outer surface of the distal end portion of the at least one additional dilator tube into the disc space and engaging the outer surface of the distal end portion with the endplate surfaces of the adjacent vertebrae to incrementally increase the height of the disc space to a distracted disc space height; removing each of the dilator tubes except for an outermost dilator tube; and inserting at least one spinal implant, the spinal implant comprising a screw engageable therewith for expanding the spinal implant within the disc space, through the outermost dilator tube and into the disc space to maintain the disc space substantially at the distracted disc space height.

10. The method of claim 9, further comprising:
positioning a distal end portion of a guide member into the disc space; and
guiding the first dilator tube along the guide member prior to inserting the distal end portion of the first dilator tube into the disc space.

11. The method of claim 10, wherein the guide member has an outer diameter sized slightly smaller than an inner diameter of the first dilator tube to facilitate the guiding.

12. The method of claim 10, wherein the guide member comprises a guide needle.

13. The method of claim 9, wherein each of the additional dilator tubes has an inner diameter sized slightly larger than an outer diameter of the preceding dilator tube to facilitate guiding of the distal end portion of each of the additional dilator tubes into the disc space.

14. The method of claim 9, further comprising successively passing at least two additional dilator tubes over a preceding dilator tube and inserting the distal end portion of each of the additional dilator tubes into the disc space and engaging the distal end portion with the adjacent vertebrae to incrementally increase the height of the disc space to the distracted disc space height.

15. The method of claim 9, wherein the sequentially increasing outer dimensions of the plurality of dilator tubes comprise sequentially increasing outer diameters.

16. The method of claim 9, further comprising:
increasing the distracted disc space height to a maximum disc space height after the inserting of the at least one spinal implant into the disc space.

17. The method of claim 9, further comprising:
making a surgical incision to provide access to the disc space, the surgical incision having a length; and
inserting the distal end portion of the first dilator tube through the surgical incision and into the disc space, the distal end portion of the first dilator tube having an outer dimension substantially equal to the length of the surgical incision.

18. The method of claim 9, further comprising determining if the disc space is at a desired disc space height prior to the step of successively passing the at least one additional dilator tube over the preceding dilator tube and inserting the distal end portion of the at least one additional dilator tube into the disc space.

19. The method of claim 9, further comprising observing the inserting of the distal end portion of each of the dilator tubes into the disc space under imaging techniques including fluoroscopy.

20. The method of claim 9, further comprising monitoring an insertion depth of the dilator tubes into the disc space during the inserting.

21. The method of claim 9, further comprising:
performing the method on a first lateral side of the patient's spine to distract the disc space on the first lateral side to a first distracted height; and
performing the method on a second lateral side of the patient's spine to distract the disc space on the second lateral side to a second distracted height substantially equal to the first distracted height.

22. The method of claim 21, further comprising:
inserting a first spinal implant into the disc space on the first lateral side having the first distracted height; and
inserting a second spinal implant into the disc space on the second lateral side having the second distracted height.

23. A method for distracting an intervertebral disc space between adjacent vertebrae, comprising:
providing a first dilator tube defining a proximal end portion, a distal end portion and an outer surface extending therebetween;
inserting the distal end portion of the first dilator tube into the disc space and engaging the outer surface of the distal end portion of the first dilator tube with endplate surfaces of the adjacent vertebrae to increase the height of the disc space to a first distracted height;
providing a second dilator tube defining a proximal end portion, a distal end portion and an outer surface extending therebetween
passing the second dilator tube over the first dilator tube; and
inserting the outer surface of the distal end portion of the second dilator tube into the disc space and engaging the outer surface of the distal end portion of the second dilator tube with the endplate surfaces of the adjacent vertebrae to incrementally increase the height of the disc space to a second distracted height; removing each of the dilator tubes except for an outermost dilator tube; and inserting at least one spinal implant, the spinal implant comprising a screw engageable therewith for expanding the spinal implant within the disc space, through the outermost dilator tube and into the disc space to maintain the disc space at a distracted height.

24. The method of claim 23, further comprising:

passing a third dilator tube over the second dilator tube; and inserting a distal end portion of the third dilator tube into the disc space and engaging the distal end portion of the third dilator tube with the adjacent vertebrae to incrementally increase the height of the disc space to a third distracted height.

25. The method of claim 23, further comprising:

passing at least one additional dilator tube over a preceding dilator tube; and inserting a distal end portion of the at least one additional dilator tube into the disc space and engaging the distal end portion of the at least one additional dilator tube with the adjacent vertebrae to incrementally increase the height of the disc space to a desired distracted height.

26. The method of claim 23, further comprising:

positioning a distal end portion of a guide member into the disc space; and guiding the first dilator tube along the guide member prior to the inserting of the distal end portion of the first dilator tube into the disc space.

27. The method of claim 23, increasing the distracted disc space height to a maximum disc space height after the inserting of the at least one spinal implant into the disc space.

* * * * *